(12) United States Patent
Floto et al.

(10) Patent No.: US 11,685,894 B2
(45) Date of Patent: Jun. 27, 2023

(54) SYSTEM FOR IDENTIFYING AND PICKING SPECTRALLY DISTINCT COLONIES

(71) Applicant: Molecular Devices, LLC, San Jose, CA (US)

(72) Inventors: Timothy Arthur Floto, Scotts Valley, CA (US); Alison Amy Glaser, Philadelphia, PA (US); Michael George Youngquist, Palo Alto, CA (US); Fiona Lucy Plows, Redwood City, CA (US)

(73) Assignee: Molecular Devices, LLC, San Jose, CA (US)

( * ) Notice: Subject to any disclaimer, the term of this patent is extended or adjusted under 35 U.S.C. 154(b) by 1151 days.

(21) Appl. No.: 16/286,888

(22) Filed: Feb. 27, 2019

(65) Prior Publication Data
US 2019/0194596 A1  Jun. 27, 2019

Related U.S. Application Data

(63) Continuation of application No. 15/115,992, filed as application No. PCT/US2015/012647 on Jan. 23, 2015, now Pat. No. 10,253,292.
(Continued)

(51) Int. Cl.
*C12M 1/00* (2006.01)
*G01C 3/32* (2006.01)
(Continued)

(52) U.S. Cl.
CPC .............. *C12M 47/04* (2013.01); *C12M 1/34* (2013.01); *C12M 31/00* (2013.01); *C12M 41/46* (2013.01);
(Continued)

(58) Field of Classification Search
CPC ........ C12M 1/34; C12M 31/00; C12M 41/46; C12M 47/04; G01N 21/31; G06T 1/00; G06T 5/40
(Continued)

(56) References Cited

U.S. PATENT DOCUMENTS 5,914,245 A * 6/1999 Bylina ..................... C12Q 1/34
422/50
8,068,670 B2 * 11/2011 Muschler ................... G06T 7/11
382/173
(Continued)

FOREIGN PATENT DOCUMENTS

CN       1289365        3/2001
CN      102321529       1/2012
(Continued)

OTHER PUBLICATIONS

Jones, P. et al., "Integration of image analysis and robotics into a fully automated colony picking and plate handling system", Nucleic Acid Research, 1992, vol. 20, No. 17, pp. 4599-4606.
(Continued)

*Primary Examiner* — Negussie Worku
(74) *Attorney, Agent, or Firm* — Merchant & Gould P.C.

(57) ABSTRACT

System, including methods and apparatus, for identifying and picking spectrally distinct colonies. In an exemplary method, a filter may be received in an optical path extending from a light source to a grayscale image detector. The filter may be configured to increase an intensity difference between a first type of colony and a spectrally distinct second type of colony. Colonies including both types may be received in the optical path. An image of the colonies may be obtained with the grayscale image detector. At least one
(Continued)

of the types of colony may be identified in the image. One or more colonies of the at least one type may be picked robotically.

11 Claims, 6 Drawing Sheets

Related U.S. Application Data

(60) Provisional application No. 61/935,816, filed on Feb. 4, 2014.

(51) Int. Cl.
*G06T 5/40* (2006.01)
*C12M 1/34* (2006.01)
*G01N 21/31* (2006.01)
*G06T 1/00* (2006.01)

(52) U.S. Cl.
CPC ............... *G01C 3/32* (2013.01); *G01N 21/31* (2013.01); *G06T 5/40* (2013.01); *G06T 1/00* (2013.01)

(58) Field of Classification Search
USPC .......................................... 358/474
See application file for complete search history.

(56) References Cited

U.S. PATENT DOCUMENTS

| 10,253,292 | B2* | 4/2019 | Floto | G06T 5/40 |
| 11,341,648 | B2* | 5/2022 | Wiles | G06V 10/40 |
| 2003/0179916 | A1* | 9/2003 | Magnuson | G01N 15/1463 |
| | | | | 382/128 |
| 2006/0164644 | A1 | 7/2006 | Jiang | |
| 2006/0280352 | A1* | 12/2006 | Muschler | G06T 7/0012 |
| | | | | 382/133 |
| 2010/0329536 | A1* | 12/2010 | Muschler | G06T 7/0012 |
| | | | | 382/133 |
| 2012/0028238 | A1* | 2/2012 | Richmond | B01L 3/021 |
| | | | | 435/3 |
| 2016/0142081 | A1* | 5/2016 | Blizard | G01N 33/48728 |
| | | | | 702/191 |
| 2020/0131465 | A1* | 4/2020 | Floto | G01N 21/6452 |
| 2021/0334514 | A1* | 10/2021 | Marcelpoil | G06V 20/693 |

FOREIGN PATENT DOCUMENTS

| CN | 102333884 | 1/2012 |
| CN | 102483867 | 5/2012 |
| CN | 103518224 | 1/2014 |
| WO | 01/22080 | 3/2001 |
| WO | 2008/109479 | 9/2008 |
| WO | 2012152768 | 11/2012 |

OTHER PUBLICATIONS

GE Healthcare Handbook—Imaging-Principles and Methods, Jun. 2012, published by GE Healthcare Bio-sciences, AB, Bjorkgatan 30, 75184 Uppsala, Sweden, total pp. 1-182.
PCT International Preliminary Reporton Patentability in Application PCT/US2015/012647, dated Aug. 18, 2016, 7 pages.
European Extended Search Report in Application 15746952.9, dated Sep. 29, 2017, 6 pages.
International Search Report and Written Opinion for PCT/B2015/012647 dated Apr. 27, 2015.
Zhang, Chengcui et al., 'An automated bacterial colony counting system'. In: 2008 IEEE International Conference on Sensor Networks. Ubiquitous and Trustworthy Computing, IEEE, 2008, pp. 233-240.

* cited by examiner

SYSTEM FOR IDENTIFYING AND PICKING SPECTRALLY DISTINCT COLONIES

CROSS REFERENCE TO RELATED APPLICATION(S)

This application is a continuation of U.S. patent application Ser. No. 15/115,992, now U.S. Pat. No. 10,253,292, filed on Aug. 2, 2016, which claims the benefit of U.S. Provisional Patent Application Ser. No. 61/935,816, filed Feb. 4, 2014. The content of these applications are incorporated by reference herein in their entirety.

BACKGROUND

Color screening can be utilized for colonies grown in the laboratory to distinguish different types of colonies. For example, a blue/white (binary) color screen exploits a visible color difference between blue colonies and white colonies to identify colonies of interest for isolation and further study or processing.

The blue/white screen is typically conducted as an in situ beta-galactosidase assay. A gene encoding full-length beta-galactosidase (or a complementing portion thereof) may be introduced into a beta-galactosidase-deficient microorganism. Colonies of the microorganism expressing the gene have beta-galactosidase activity, whereas colonies that do not express the gene do not have the activity. These two types of colonies can be distinguished by growing the colonies in the presence X-gal, a substrate for beta-galactosidase. Hydrolysis of X-gal by beta-galactosidase converts the colorless substrate to a blue dye, which turns expressing colonies blue. In contrast, non-expressing colonies do not accumulate the blue dye and remain white.

Colony analysis systems are available for detecting images of colonies. However, these systems often are equipped with a grayscale ("black-and-white") image detector. The grayscale image detector obtains an image by measuring of an amount of light incident on each pixel without recording the wavelength or color of that light. As a result, colony types of different color may not be reliably distinguishable in the image. Colonies of at least one type may be missed partially or completely or may be incorrectly identified as belonging to another type.

Better colony analysis systems are needed for identifying colonies of different color based on images obtained by a grayscale image detector.

SUMMARY

The present disclosure provides a system, including methods and apparatus, for identifying and picking spectrally distinct colonies. In an exemplary method, a filter may be received in an optical path extending from a light source to a grayscale image detector. The filter may be configured to detect an intensity difference between a first type of colony and a spectrally distinct second type of colony. Colonies including both types may be received in the optical path. An image of the colonies may be obtained with the grayscale image detector. At least one of the types of colony may be identified in the image. One or more colonies identified may be picked robotically.

DETAILED DESCRIPTION

Figure 1:
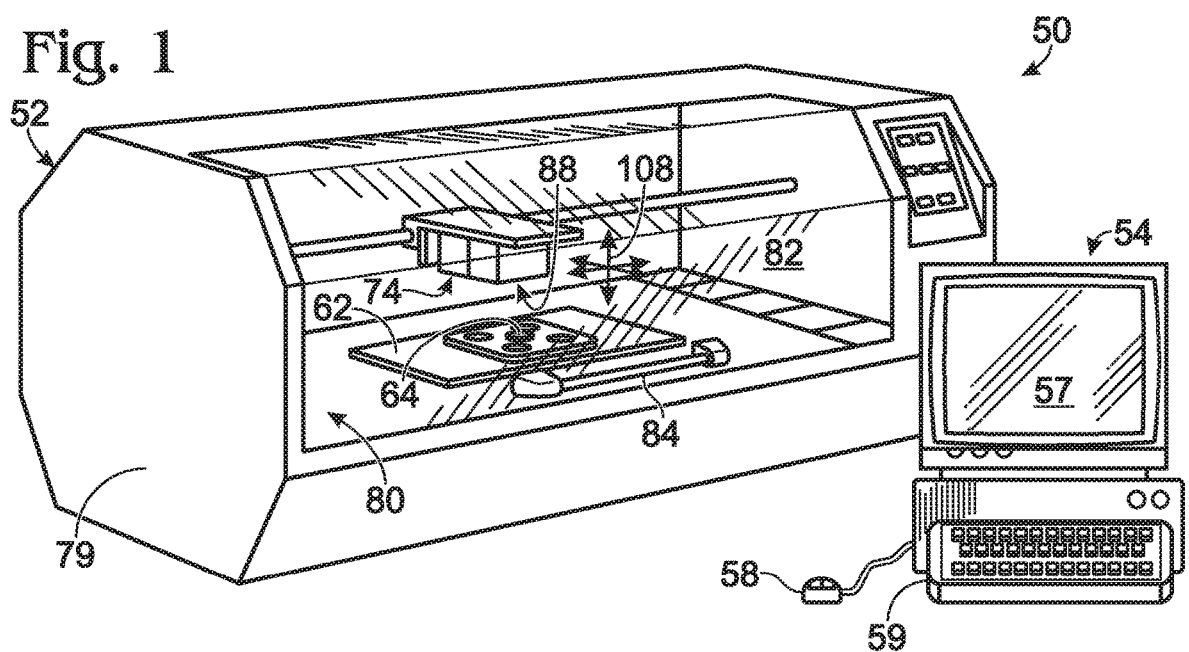
FIG. 1 is a perspective view of an exemplary embodiment of a picking system for identifying and isolating spectrally distinct colonies, with a container disposed in an examination region of the system and including a medium supporting at least two types of spectrally distinct colonies, in accordance with aspects of the present disclosure.

The present disclosure provides a system, including methods and apparatus, for identifying and picking spectrally distinct colonies. In an exemplary method, a filter may be received in an optical path extending from a light source to a grayscale image detector. The filter may be configured to increase an intensity difference between a first type of colony and a spectrally distinct second type of colony. Colonies including both types may be received in the optical path. An image of the colonies may be obtained with the grayscale image detector. At least one of the types of colony may be identified in the image. One or more colonies of the at least one type identified may be picked robotically.

An exemplary method of isolating colonies is provided. In the method, a spectral filter may be received in an optical path extending from a light source to a grayscale image detector. The filter may be configured to selectively decrease an intensity of a blue colony relative to a white colony. A medium and colonies supported by the medium may be received in the optical path. The colonies may include at least one blue colony and at least one white colony. An image may be obtained with the grayscale image detector by detecting light received from the colonies and the medium, with the filter selectively decreasing an average intensity of one or more blue colonies relative to an average intensity of the medium and one or more white colonies. A histogram of intensity values for pixels in the image may be created. One or more blue colonies may be identified in the image based on a subset of the pixels selected from the histogram. At least one of the blue colonies may be picked robotically.

An exemplary system for identifying and isolating spectrally distinct colonies is provided. The system may comprise a detection system defining an optical path extending from a light source to a grayscale image detector. The system also may comprise a filter disposed in the optical path and configured to increase an intensity difference between a first type of colony and a spectrally distinct second type of colony. The system further may comprise of a stage to support a container containing colonies including the first type and the second type. The system even further may comprise a picking device and a data processing system. The data processing system may be configured (i) to receive an image of the colonies from the image detector, (ii) to identify at least one of the types of colony in the image, and (iii) to instruct the picking device to robotically pick one or more colonies of the at least one type identified.

Further aspects of the present disclosure are presented in the following sections: (I) exemplary picking system, (II) exemplary images, histograms, and filters, (III) exemplary pixel selection with a graphical user interface, (IV) methods of colony identification/isolation, and (V) examples.

I. Exemplary Picking System

This section describes aspects of an exemplary picking system 50 for identifying and isolating spectrally distinct colonies; see FIGS. 1-5. The system interchangeably may be termed a colony analysis system, a colony identification system, or a colony isolation system.

Figure 2:
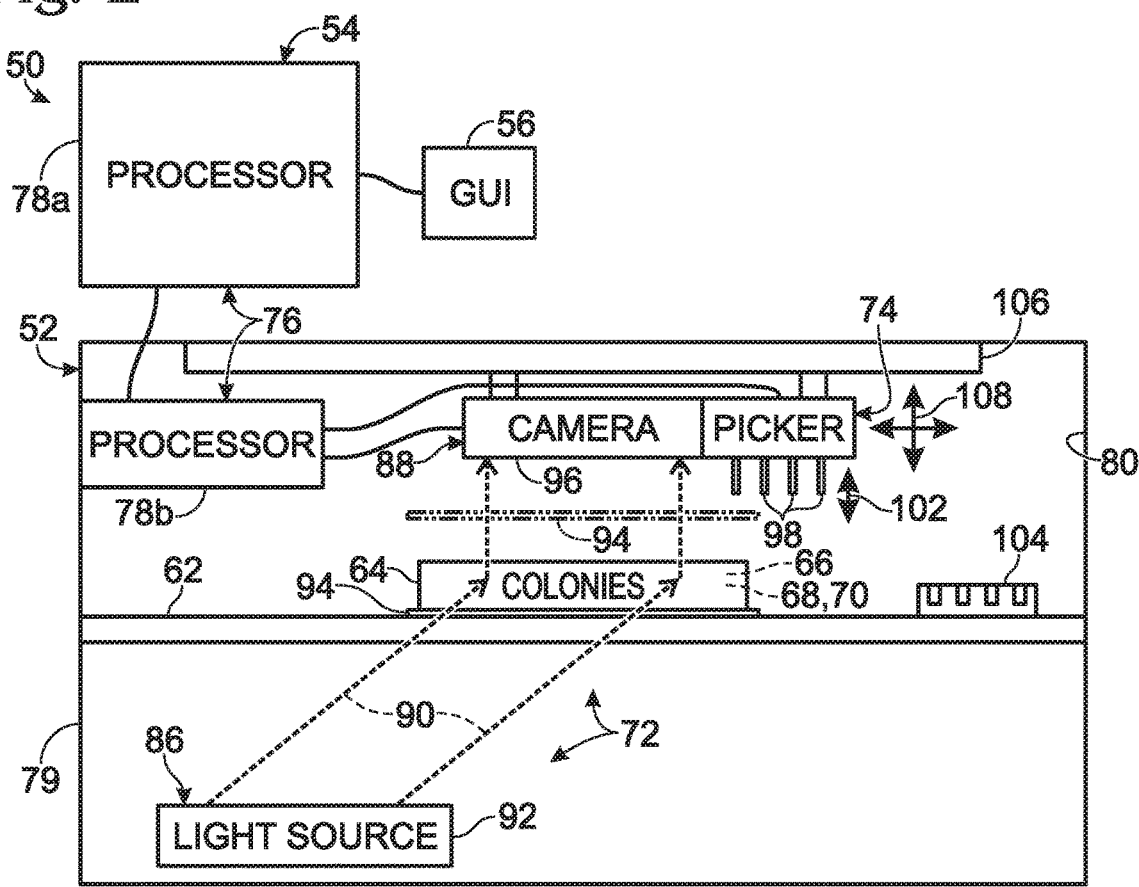
FIG. 2 is a schematic view of selected aspects of the system of FIG. 1, in accordance with aspects of the present disclosure.

FIGS. 1 and 2 show selected aspects of picking system 50. The picking system may include an instrument 52 in communication with an external computing device 54 (e.g., a personal desktop computer, tablet, laptop, smartphone, etc.), or computing device 54 may be integral to the instrument. Computing device 54 may have any suitable wired or wireless connection to instrument 52. The computing device and/or instrument 52 may include at least one graphical user interface (GUI) 56 for interaction with a user. The GUI may include a display 57, and one or more user input devices, such as a mouse 58, a keyboard 59, a keypad, a joystick, a touchscreen on the display, or any combination thereof, among others.

Instrument 52 may include a stage 62 to support one or more containers 64 that each contain a medium 66 (e.g., a solid, semi-solid, or liquid medium) supporting at least two types of spectrally distinct colonies 68, 70. The picking system also may include an optical detection system 72 to obtain one or more images of the contents of each container 64, particularly images of medium 66 and colonies 68, 70. The picking system further may include a picking device 74 (a "picker") to robotically pick identified colonies. The picking system even further may include a data processing system 76 including one or more processors 78a, 78b (interchangeably termed controllers). The data processing system may be in communication with and/or may control optical detection system 72 and picking device 74, may process image data, and may interact with a user via graphical user interface 56.

Any suitable combination of detection system 72, picking device 74, and data processing system 76, and/or any combination of components thereof, may be located inside a housing 79 of system 50 (see FIG. 1). The housing may surround a chamber 80 containing stage 62. The chamber may be opened and closed by operation of a transparent door 82, which may have a handle 84. The use of a chamber to isolate contents of the chamber from the ambient environment minimizes contamination of colonies as the colonies are being imaged and/or picked (e.g., when container 64 is open on top).

Detection system 72 may include an illumination portion 86 that irradiates (i.e., illuminates) stage 62 and container 64 with light (e.g., visible light), and a detection portion 88 that detects light received from the contents of container 64, particularly colonies and a medium in the container (see FIG. 2). The detection system may define an optical path 90 on which light travels from the illumination portion to the detection portion. Each container 64 may be disposed in the optical path, such that at least a portion of the medium, and at least a subset of the colonies supported by the medium, are irradiated by illumination portion 86 and imaged by detection portion 88.

Illumination portion 86 may include a light source 92 and, optionally, input optics configured to direct and/or modify light from the light source. The light source may provide broad-spectrum visible light, also termed white light. In any event, the light source may produce at least one wavelength and/or waveband of light that is differentially absorbed (and thus differentially transmitted) by the two types of colonies relative to each other. Also, the illumination portion may illuminate the stage and colonies 68, 70 with at least one wavelength and/or waveband of light that is differentially absorbed by the two types of colonies.

Illumination portion 86 may be offset from detection portion 88, as shown, to provide dark-field illumination of at least a portion of container 64 and at least a portion of its contents. For example, light from illumination portion 86 may travel to the stage at an angle of about 30 to 60 degrees or about 45 degrees, among others, and may travel to detection portion 88 on a portion of optical path 90 that is orthogonal to stage 62. The light that travels from the colonies and medium to the detection portion may be at least predominantly scattered light. In other embodiments, illumination portion 86 may provide bright-field illumination or any other type of illumination.

Light source 92 may include any suitable lamp or combination of lamps. Exemplary lamps that may be suitable include electroluminescent lamps (e.g., light-emitting diodes, light-emitting electrochemical cells, electroluminescent sheets, and electroluminescent wires, among others), gas discharge lamps (e.g., fluorescent lamps, cathode lamps, plasma lamps, inert-gas lamps), high-intensity discharge lamps, incandescent lamps, or the like. In exemplary embodiments, the light source may include an array of lamps, such as an array of light-emitting diodes. For example, the array may be formed by at least one row of light-emitting diodes, a pair of rows forming a two-dimensional array, a three-dimensional array, or the like.

The input optics, in any, of the illumination portion may, for example, include any combination of one or more optical elements, such as lenses, mirrors, gratings, prisms, light guides, light homogenizers/mixers, filters, or the like. In the depicted embodiment, the input optics include a spectral filter 94, which filters light from the light source after the light reaches stage 62 and before the light reaches container 64. In other embodiments, filter 94 may be included in detection portion 88 of detection system 72, as shown in phantom outline above container 64 in FIG. 2. In some embodiments, filter 94 may be provided by a plurality of filter elements. The filter elements may or may not be attached to one another. In some examples, the filter elements may be spaced from each other, such as with one or more filter elements in illumination portion 86 on the optical path between the light source and the colonies, and one or more other filter elements may be in detection portion 88 on the optical path between the colonies and an image detector.

Detection portion 88 may be configured to receive light from container 64 and particularly from at least a portion of the medium and a subset of the colonies therein. The detection portion may include a grayscale image detector 96 and associated optics to form a camera. The optics may include any combination of the optical elements listed above for illumination portion 86, such as a spectral filter 94 operatively disposed between container 64 and image detector 96 to block a portion of light received from the container's contents, in a wavelength-dependent manner.

The image detector may be any suitable optical sensing device with spatial resolution to allow creation of an image. The image detector may be sensitive to optical radiation, namely, ultraviolet radiation, visible light, or infrared radiation, or any combination thereof. Suitable image detectors for the detection portion may include a charge-coupled device (CCD) array, a complementary metal-oxide semiconductor (CMOS) array, a charge-injection device (CID) array, a photodiode array, any array of photomultiplier tubes (PMTs), an array of pin photodiodes, an array of avalanche photodiodes, photocells, phototubes, and the like. Alternatively, the image detector may have one or more photosensitive elements (e.g., CCD elements, CMOS elements, photodiodes, etc.) that are moved in one or more dimensions to obtain the image by scanning a field of view.

The image detector is described as "grayscale" because the detector obtains intensity data for pixels of an image without acquiring information that spectrally distinguishes the pixels of the image from one another. In other words, the detector obtains a measure of an amount of light incident on each pixel without recording the wavelength or color of that light. Images obtained by the image detector may be described as "grayscale" images, whether or not the images are displayed in shades of gray.

Picking device 74 may be or include any device or set of devices capable of picking colonies with one or more picking elements, such as one or more picking pins. In the depicted embodiment, the picking device includes a picking head equipped with a plurality of picking pins 98. The picking device may have an array of picking pins, such as 96 pins arranged in an array that matches the wells of a 96-well microplate. Each pin may be independently extendable along a vertical axis 102, for contact with a colony to transfer at least a portion of the colony to the pin, and independently retractable along the same axis. The picking device may pick one or more colonies from sample container 64 and transfer at least a portion of the picked colony to a destination container 104. "Picking a colony," as used herein, means that at least a portion of the colony is removed and transferred elsewhere.

Each of picking device 74 and image detector 96 (or the camera) may be movable with respect to stage 62. Picking device 74 and image detector 96 may be driven by a drive system 106 along a left-right axis, a vertical axis, a forward-rearward axis, or any combination thereof, indicated at 108. The picking device and the image detector may be fixed relative to each other, such that the picking device and the detector travel along each axis as a unit. With this arrangement, the horizontal offset of each picking pin from each image pixel is fixed, which allows the horizontal offset of each pin from each colony to be determined. The determined positional relationship between each pin and each colony to be picked allows optimal utilization of the pins during a picking procedure using multiple pins to pick up multiple colonies. In other embodiments, the picking device and the image detector may travel separately and may be driven independently along each axis.

Data processing system 76 may include a single processor (also termed a controller) or a plurality of processors (e.g., processors 78a and 78b) that collectively are in communication with and/or control operation of image detector 96, pins 98 of picking device 74, drive system 106, GUI 56, and the like. If a plurality of processors are present in the system, the processors may communicate with each other at any suitable time. Each processor may be described as a computing device and may, for example, include a digital processor, memory for storage of data/algorithms/instructions, one or more IO ports, a user interface, etc. The processor may be a dedicated component of the system or may, for example, be a personal computer with multi-purpose functionality. In some cases, the processor may be configured as a controller that controls, monitors, and/or coordinates operation of other system components.

Any suitable containers 64 may be used. Exemplary containers include petri dishes, square plates, flasks, multi-well plates, and the like. Exemplary petri dishes that may be suitable have a diameter of 30, 60, 100, 140, or 200 mm, among others. Suitable containers generally are open (or openable) on top, such as having a lid or cover that can removed to provide access to the contents of the container, at least when colonies are picked.

Each type of colony may be formed by any suitable microorganism or cells. Exemplary microorganisms that may form microbial colonies include viruses, bacteria, protozoans, yeast, and single-celled algae, among others. Exemplary cells from multi-celled organisms (e.g., macro-organisms) that may form the colonies include plant cells and animal cells. Viral colonies, interchangeably termed viral plaques, may, for example, be formed by regions of lysis within a lawn of cells, such as a lawn of bacterial cells, animal cells, or plant cells. Members of a given colony may (or may not) be clonal relative to one another.

Figure 3:
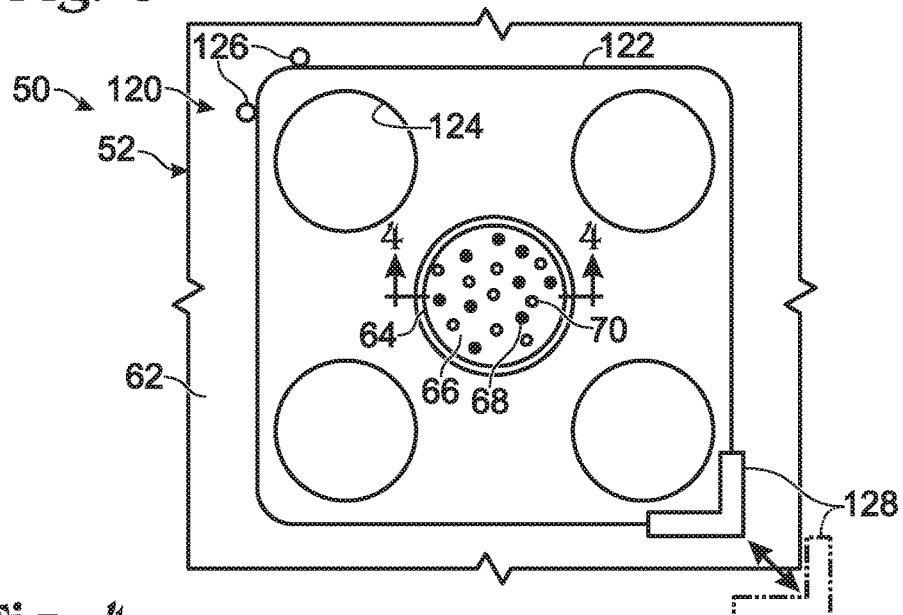
FIG. 3 is a plan view of the examination region and container of FIG. 1.

FIG. 3 shows an examination region 120 of instrument 52, with the examination region being formed in part by stage 62. The examination region of the instrument may be where one or more containers are supported, and colonies are imaged and picked. The examination region may include any suitable combination of devices and structures for supporting and, optionally, restricting lateral movement of, each container. For example, the examination region may include stage 62 (interchangeably termed a support member, a platform, or a table) disposed under each of the containers. The stage may be formed at least partially of a material (e.g., a colorless, transparent material) that is optically transmissive for broad spectrum visible light, and/or the stage may define one or more aperture under the containers to allow passage of light.

The examination region also may include a holder or tray 122 supported by stage 62. The holder may define one or more openings 124 to receive one or more containers 64 (only one container is shown here). The holder may limit horizontal movement of the container after the container is received in one of openings 124. The instrument may be supplied with a plurality of interchangeable holders or trays that are configured to accommodate different sizes and/or shapes of containers 64. Holder 122 may be held in place on the stage by a clamp mechanism, such as formed by a pair of pins 126 and an adjustable corner piece 128 disposed diagonally opposite the pins. The holder may be optically opaque. The holder may have a thickness that is less than the height of the container to facilitate removal of the container from the holder.

Figure 4:
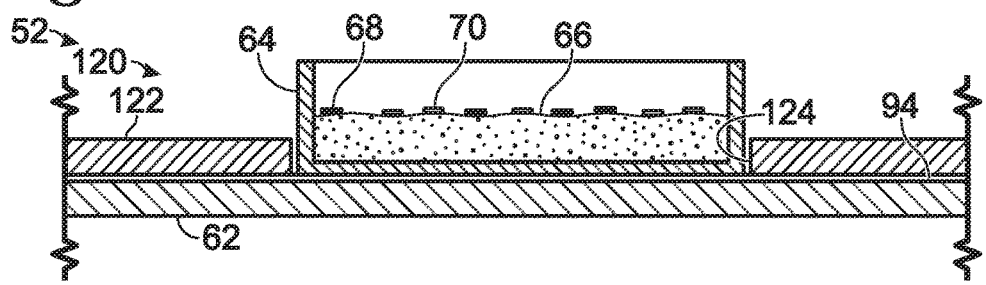
FIG. 4 is a fragmentary sectional view of the examination region and container of FIG. 1, taken generally along line 4-4 of FIG. 3 in the presence of an exemplary spectral filter that increases a detected intensity difference between spectrally distinct colonies.

FIG. 4 shows a cross-sectional view of examination region 120 and container 64. Filter 94 may be sandwiched between stage 62 and holder 122. Accordingly, to install filter 94, the filter may be placed onto stage 62 before holder 122 is attached to the stage over the filter. The filter may laterally span each opening 124 of the holder, with container 64 disposed over and, optionally, in contact with the filter. As a result, light from the light source may travel through the stage, through filter 94, to reach medium 66 and colonies 68, 70. A portion of the light may be scattered by the medium and the colonies towards the grayscale image detector.

Figure 5:
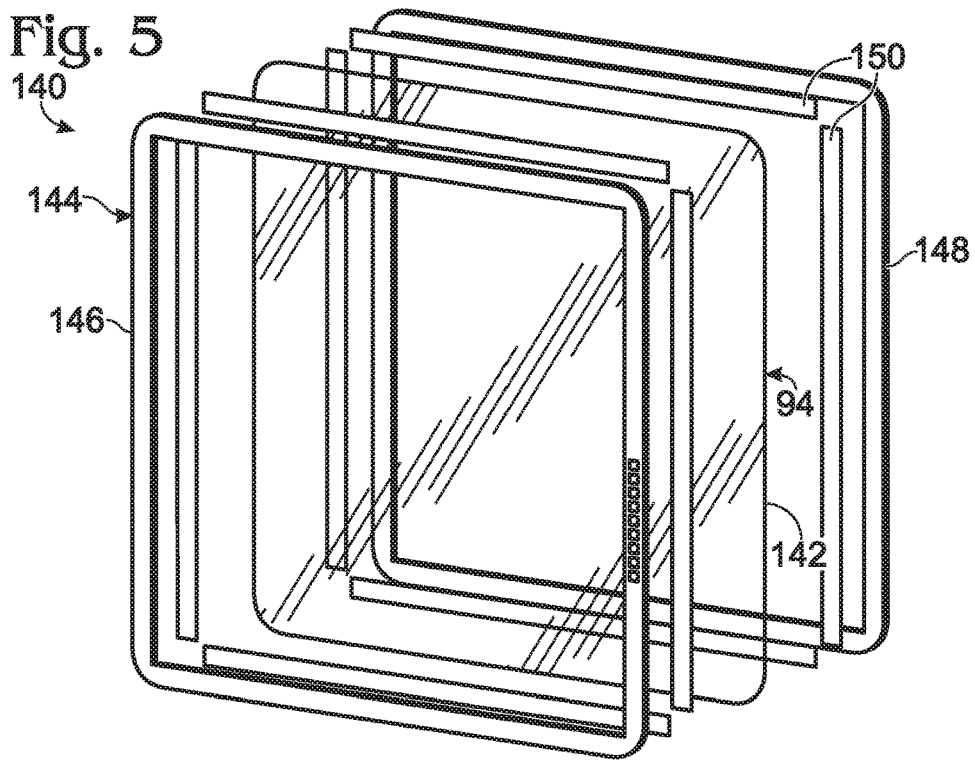
FIG. 5 is an exploded view of an exemplary filter assembly that may provide the filter of FIG. 4, taken in isolation from other system components.

FIG. 5 shows an exemplary filter assembly 140 that provides filter 94. Filter 94 may be formed by at least one filtering sheet 142. The filtering sheet may be attached to a frame 144 having a front piece 146 and a back piece 148. Each frame piece may be attached by an adhesive, such as adhesive strips 150 that are sandwiched between sheet 142 and the frame piece. The frame assembly may have the same footprint as holder 122 (see FIG. 3).

II. Exemplary Images, Histograms, and Filters

This section describes exemplary images and histograms that may be obtained and created by system 50, and exemplary filters for the system; see FIGS. 6-12.

Figure 6:
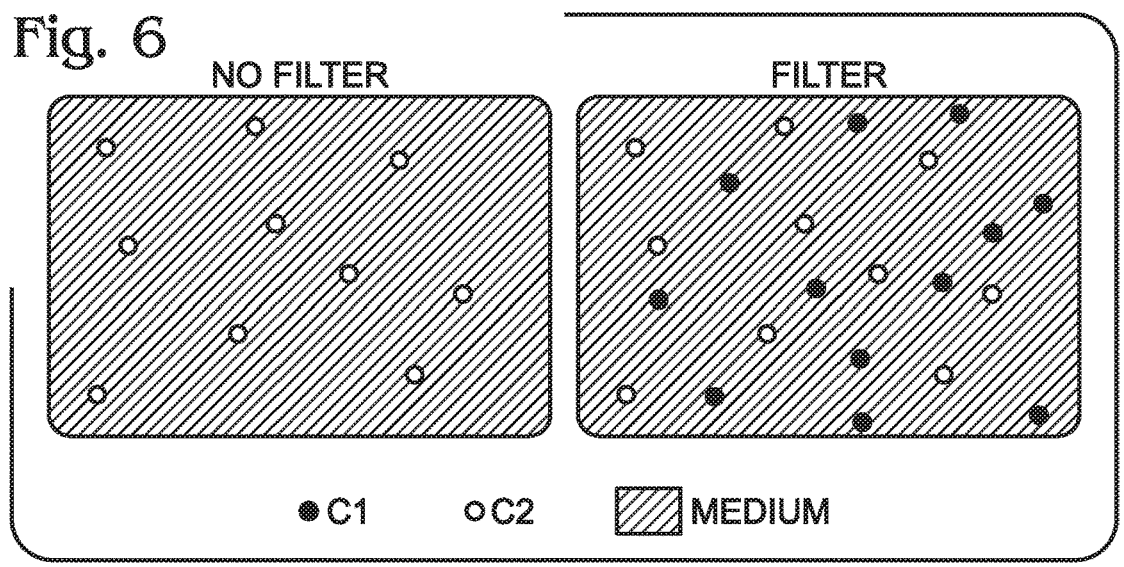
FIG. 6 is a pair of corresponding grayscale images that each may be obtained by the grayscale image detector of the system of FIG. 1 with the same colonies and field of view, but respectively without and with a spectral filter in the optical path, with each image showing the intensity of light detected from spectrally distinct types of colonies (C1 and C2) and from a medium (M) intermediate the colonies, in accordance with aspects of the present disclosure.

FIG. 6 shows a pair of corresponding intensity images that may be obtained by the grayscale image detector of system 50 from a same field of view. The field of view contains two types of spectrally distinct colonies (C1 and C2) of different color, supported by a medium (M). The left-side image may be obtained without spectral filter 94, and the right-side image may be obtained with the filter. Comparison of the two images reveals that the C1 colonies cannot be distinguished from background (M) without the filter. In other words, the C1 colonies are not visible in the left-side image, but become identifiable in the presence of the spectral filter. In less extreme cases, a subset of the C1 colonies are distinguishable from the background and the remainder are not.

Figure 7:
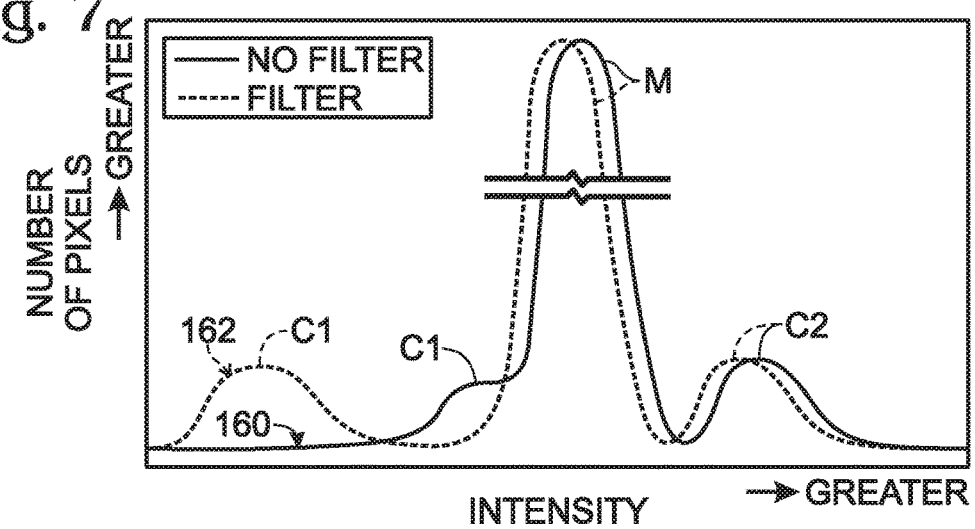
FIG. 7 shows a pair of schematic histograms that may be obtained by plotting pixel data from the images of FIG. 6 and showing the number of pixels having various intensities of detected light in each of the images.

FIG. 7 shows a pair of schematic histograms 160, 162 that may be obtained by plotting pixel data from the images of FIG. 6. Histogram 160 is a schematic plot of the number of pixels present in each intensity increment, for the full range of intensities of all of the pixels in the left-side image of FIG. 6. Histogram 162 is a corresponding schematic plot for the right-side image of FIG. 6. The pixel populations produced by each type of colony (C1 and C2) and the medium (M), where the medium is not overlapped by either type of colony, are labeled for each histogram.

The pixels from both images of FIG. 6 produce an M peak and a C2 peak that are resolved from each other. The M peak is much taller than the C2 peak, because most of the pixels in each image represent a region of the medium intermediate the colonies. Accordingly, the size of the M peak is generally determined by the size and density of the colonies growing on and/or in the medium and may, for example, be at least 10, 25, or 100 times the height of the colony peaks. The filter used has only a small effect on the average intensity of the M and C2 pixels (and has a larger effect on the average intensity of the C1 pixels).

The C1 pixels from the no-filter image of FIG. 6 are not resolved from the M pixels in histogram 160, because the two populations have overlapping intensity distributions. Accordingly, here, the C1 pixels form a shoulder on the M peak, rather than a resolved peak like the C2 pixels. As a consequence, all of the C1 colonies cannot be reliably identified from histogram 160. In contrast, the C1 pixels from the image obtained in the presence of a spectral filter form a distinct C1 peak in histogram 162. The spectral filter increases the intensity difference between the C1 and C2 pixels, and between the C1 and M pixels. These increases are achieved by selectively reducing the average intensity of the C1 pixels relative to the average intensity of the M pixels and C2 pixels. In other examples, the C1 pixels may have about the same intensity as the M pixels or may have a higher average intensity than the M pixels, which may, for example, form a shoulder on the higher intensity side of the M peak or may produce an overlap with the C2 peak (see below).

Figure 8:
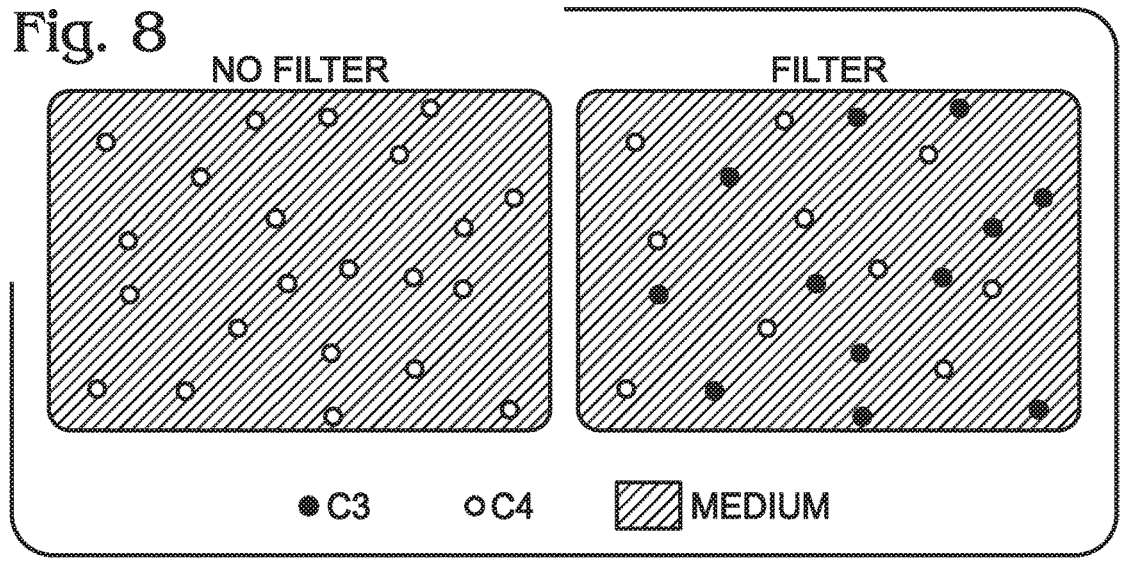
FIG. 8 is another pair of corresponding grayscale images that each may be obtained by the grayscale image detector of the system of FIG. 1 with the same colonies and field of view, but respectively without and with a spectral filter in the optical path, with each image showing the intensity of light detected from another pair of spectrally distinct types of colonies (C3 and C4) and from a medium (M) intermediate the colonies, in accordance with aspects of the present disclosure.

FIG. 8 shows another pair of corresponding intensity images that may be obtained by the grayscale image detector of system 50 from a same field of view. The field of view contains another two types of spectrally distinct colonies (C3 and C4) of different color, supported by a medium (M). The left-side image may be obtained without spectral filter 94, and the right-side image may be obtained with the filter. Comparison of the two images reveals that the C3 colonies cannot be distinguished from the C4 colonies (and vice versa) without the filter. In other words, the C3 and C4 colonies have overlapping intensity distributions without the filter, but become distinguishable with the filter. In less extreme cases, a subset of the C3 colonies are distinguishable from the C4 colonies without the filter and the remainder are not.

Figure 9:
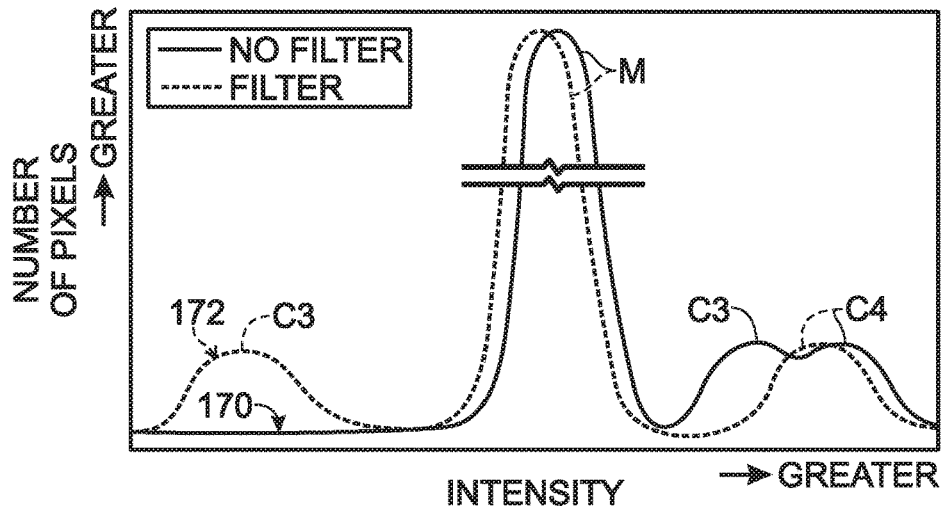
FIG. 9 shows a pair of schematic histograms that may be obtained by plotting pixel data from the images of FIG. 8 and showing the number of pixels having various intensities of detected light in each of the images.

FIG. 9 shows a pair of schematic histograms 170, 172 that may be obtained by plotting pixel data from the images of FIG. 8. Histogram 170 is a schematic plot of the number of pixels present in each intensity increment, for the full range of intensities of all of the pixels in the left-side image of FIG. 8. Histogram 172 is a corresponding schematic plot for the right-side image of FIG. 8. The pixel populations produced by each type of colony (C3 and C4) and the medium (M), where the medium is not overlapped by either type of colony, are labeled for each histogram.

The C3 and C4 pixels are resolved from the M pixels in the histogram without use of a spectral filter. Accordingly, each colony may be identifiable as a colony without the filter. However, each colony cannot be identified as a C3 colony versus a C4 colony, without the filter (see the left-side image of FIG. 9), because the C3 and C4 peaks overlap one another. However, use of a suitable spectral filter shifts the C3 peak away from the C4 peak, such as to a position of lower intensity than the M peak and resolved from both the M and C4 peaks. In other embodiments, the filter may shift the C3 peak to lower intensity and toward the M peak, to improve resolution between the C3 and C4 peaks, by positioning the C3 peak intermediate the M and C4 peaks.

Figure 10:
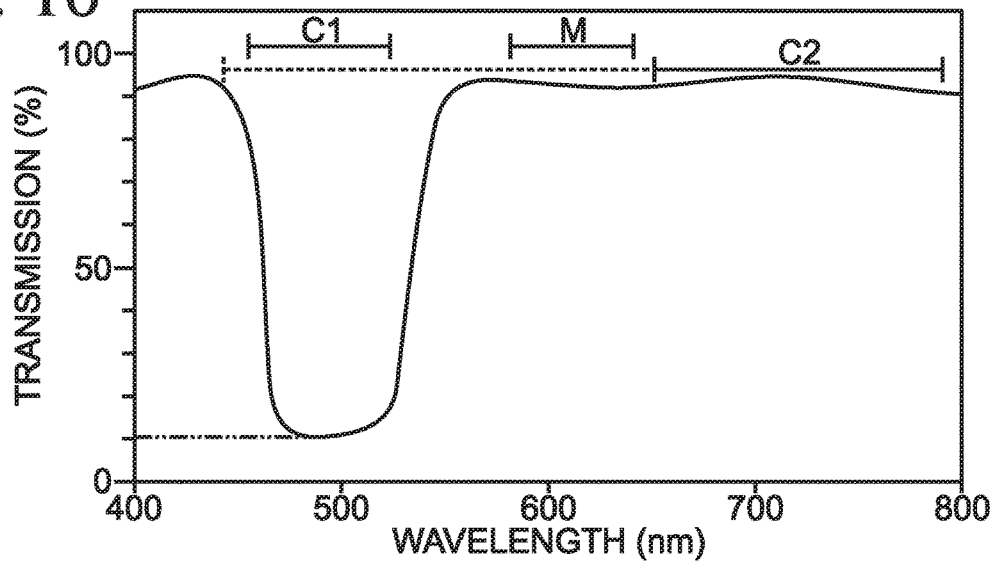
FIG. 10 is a transmission spectrum of an exemplary filter for the system of FIG. 1, with exemplary transmission ranges indicated above the spectrum for spectrally distinct colony types C1 and C2 (or C3 and C4) and the medium (M), in accordance with aspects of the present disclosure.

FIG. 10 shows a transmission spectrum of an exemplary spectral filter for system 50. Exemplary wavelength ranges for efficient transmission of light by colonies and the medium are indicated above the spectrum for spectrally distinct colony types C1 and C2 and the medium (M). Light transmission across each wavelength range indicated may average about 40%, 50%, 60%, 70%, or 80%, among others. The spectral filter efficiently transmits light at wavelengths where C2 colonies and the medium (M) also transmit efficiently, but much less so where C1 colonies transmit efficiently. The wavelength range of efficient light transmission for the C2 colonies may or may not overlap the range of the medium and/or the C1 colonies (as indicated by a dashed line extending from the C2 range). An alternative version of the shorter-wavelength region of the transmission spectrum is shown with a dash double-dot line.

Figure 11:
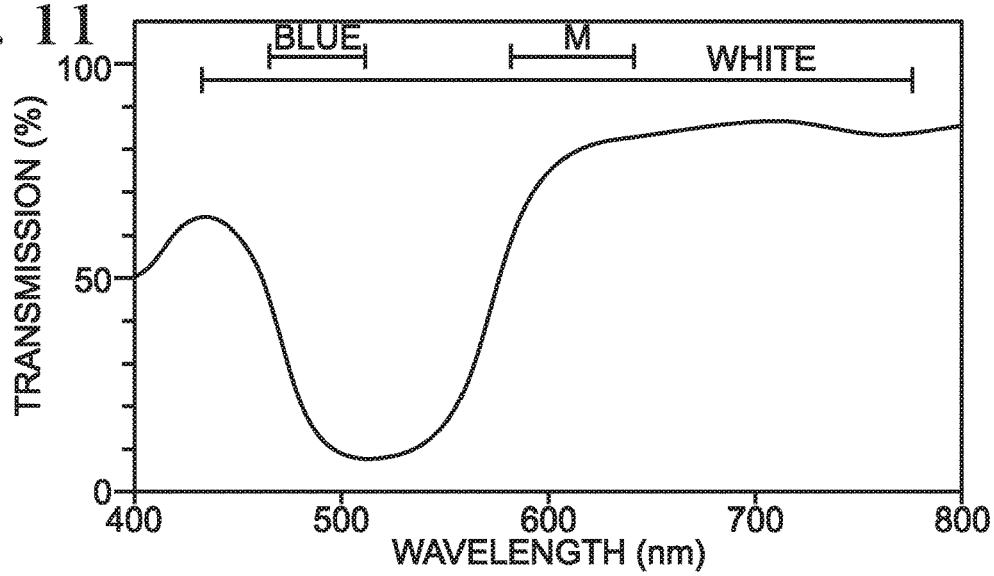
FIG. 11 is a transmission spectrum of another exemplary spectral filter for the system of FIG. 1, with exemplary transmission ranges for blue colonies, white colonies, and the medium (M) indicated above the spectrum, in accordance with aspects of the present disclosure.

FIG. 11 shows a transmission spectrum of another exemplary spectral filter for system 50. The filter of FIG. 11 may be suitable for distinguishing white colonies from blue colonies, such as when an in situ beta-galactosidase assay has been performed on the colonies. Exemplary wavelength ranges for efficient transmission (as defined for FIG. 10) of light by colonies and the medium are indicated above the spectrum for blue colonies, the medium, and white colonies. The filter selectively blocks light in the range of efficient transmission for the blue colonies relative to the medium and the white colonies, although the filter does reduce transmission for the M and white ranges, too.

Figure 12:
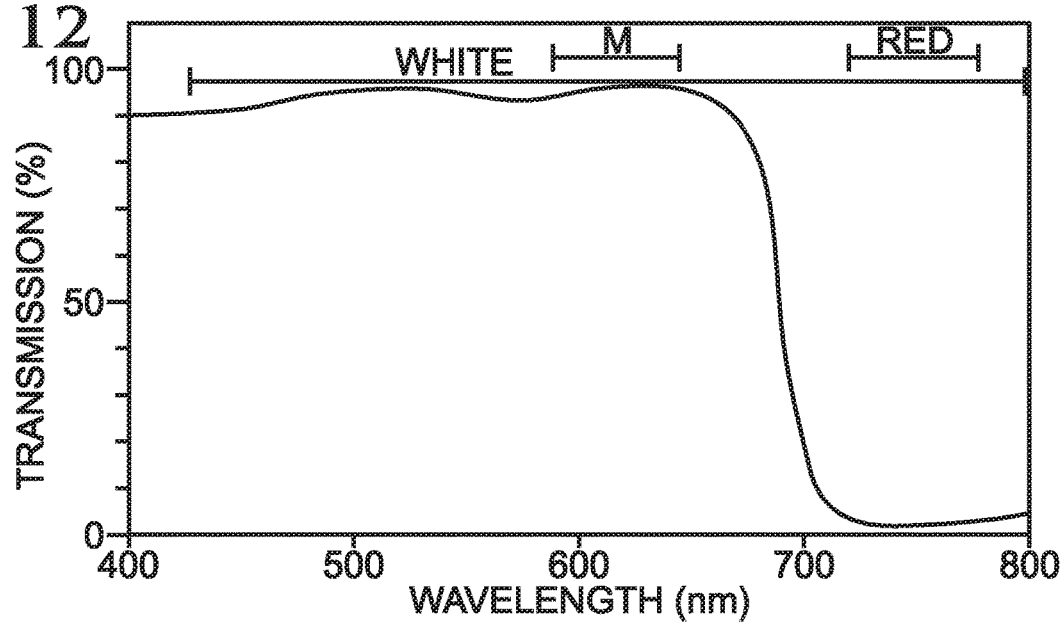
FIG. 12 is a transmission spectrum of yet another exemplary filter for the system of FIG. 1, with exemplary transmission ranges for red colonies, white colonies, and the medium (M) indicated above the spectrum, in accordance with aspects of the present disclosure.

FIG. 12 shows a transmission spectrum of another exemplary spectral filter for system 50. The filter of FIG. 12 may be suitable for distinguishing white colonies from red colonies. Exemplary wavelength ranges for efficient transmission (as defined for FIG. 10) of light by colonies and the medium are indicated above the spectrum for white colonies, the medium, and red colonies. Red colonies and white colonies may, for example, be bacterial colonies growing on a MacConkey agar medium, and able (red) or unable (white) to utilize lactose from the medium.

III. Exemplary Pixel Selection with a Graphical User Interface

Figure 13:
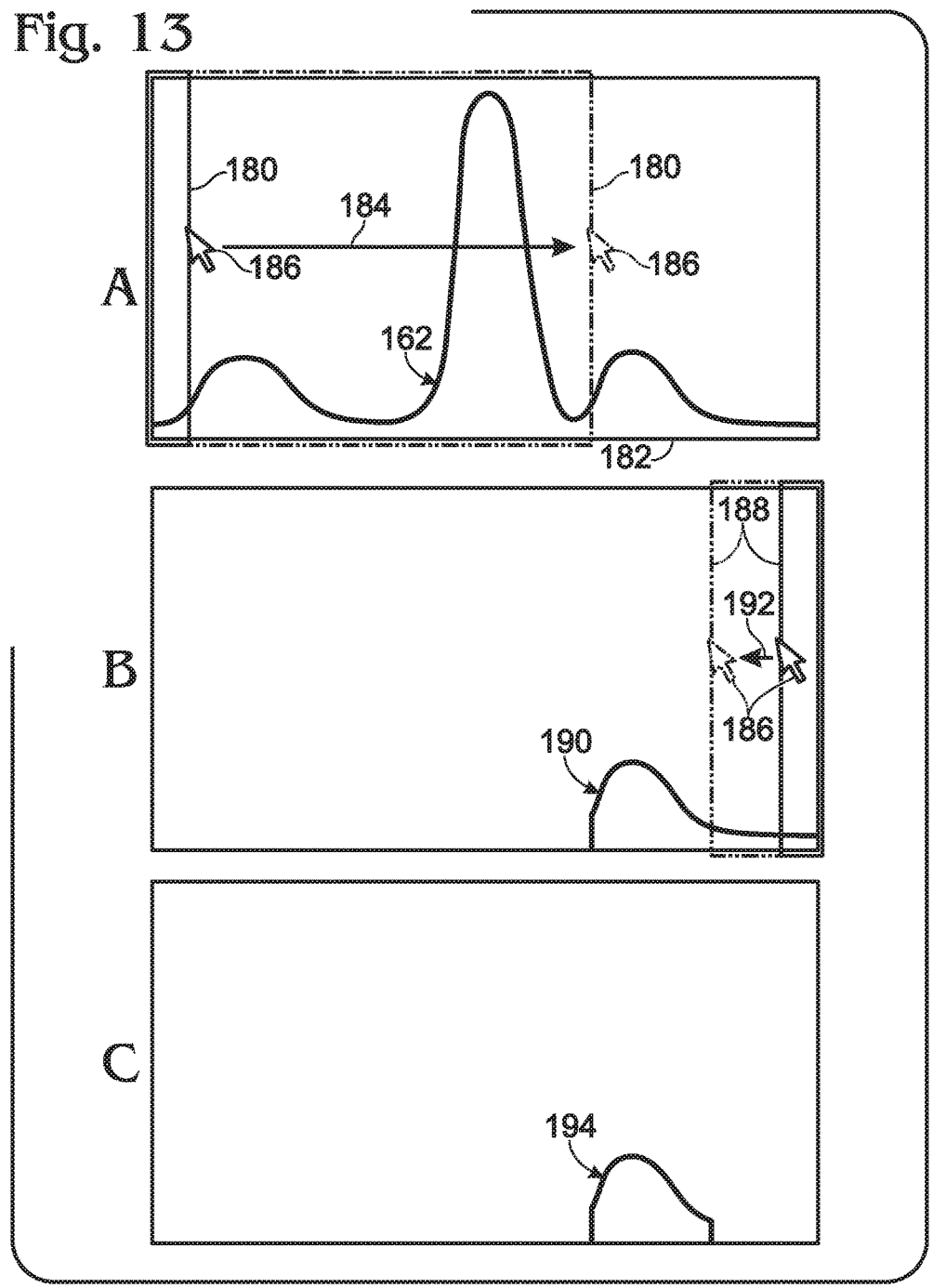
FIG. 13 shows a series of exemplary, somewhat schematic screen images (A, B, and C) that may be displayed to a user by a graphical user interface of the system of FIG. 1 as the user selects a range of intensities from one of the histograms of FIG. 7, with the range being selected for processing by a colony identification algorithm of the system to identify colonies in the selected range, in accordance with aspects of the present disclosure.
Figure 14:
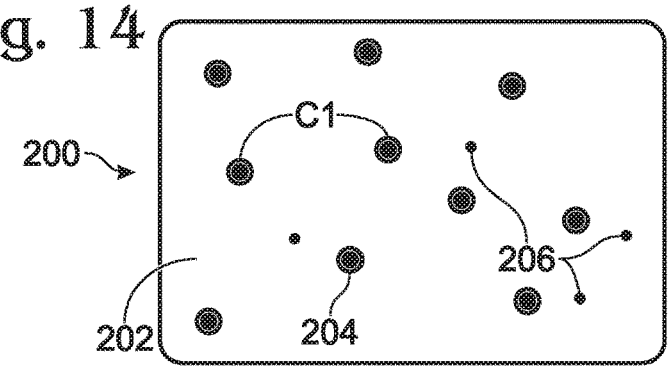
FIG. 14 is an exemplary masked (and optionally pseudo-colored) version of the right-side ("filter") image of FIG. 6 that may be displayed to the user by the graphical user interface of the system of FIG. 1 based on the intensity range selection of FIG. 13, with the displayed image showing only the pixels present in the selected range and marking each colony identified, in accordance with aspects of the present disclosure.

This section describes an exemplary graphical user interface (GUI) for the picking system of Section I, and how the GUI is used to direct colony identification; see FIGS. 13 and 14.

FIG. 13 shows a series of exemplary, somewhat schematic screen images (A, B, and C) that may be presented to a user by graphical user interface 56 of system 50 (see FIGS. 1 and 2) as the user selects a range of intensities from histogram 162 of FIG. 7.

FIG. 13A illustrates selection of a lower limit. The interface may display a low-limit selector 180 adjacent and/or overlapping histogram 162. The user may move selector 180 in a direction parallel to intensity axis 182 of the displayed histogram, indicated by an arrow at 184, to set the lower limit (or a threshold) for an intensity range. The user may slide selector 180 by moving a cursor 186 (e.g., via a mouse), pressing a key repeatedly, touching a display screen, or the like. When a desired position for the selector is reached, the user may select and enter the current position by manipulating the interface, such as by pressing a predefined key or pressing (e.g., single- or double-clicking) or releasing a button on a mouse.

FIG. 13B illustrates selection of an upper limit. Interface 56 may display a high-limit selector 188 adjacent and/or overlapping histogram 162 or a portion 190 of the histogram remaining after selection of the lower limit. The user may move selector 188, indicated at 192, to select and input another position for the selector as with the low-limit selector described above. FIG. 13C shows a portion 194 of histogram 162 remaining after the intensity range for colony identification has been selected. In the present illustration, an intensity range for the C2 colonies of FIGS. 6 and 7 has been selected. In some embodiments, only a threshold (either only a high limit or only a low limit) may be set. In some embodiments, the high limit may be set before the low limit. In some embodiments, the data processing system of the picking system may select an intensity range automatically for at least one of the colony types.

FIG. 14 shows an exemplary masked (and optionally pseudocolored) version 200 of the right-side ("filter") image of FIG. 6 that may be displayed to the user by the graphical user interface of system 50. Masked image 200 may be created based on an intensity threshold or range selection. In the present illustration, image 200 is created based on the intensity range selected in FIG. 13, which may at least predominantly represent pixels of C2 colonies (see FIGS. 6 and 7). Image 200 may pseudocolor only the pixels present in the selected range, with the remaining masked pixels displayed as a uniform, distinguishable background 202. The data processing system of system 50 may identify colonies in the pseudocolored portion of the image with an algorithm that uses any suitable criteria, such as pixel proximity, pixel cluster size, cluster shape, cluster uniformity, or any combination thereof, among others. Each identified colony may be marked, such as displayed with a distinguishable ring 204 around the colony, by changing the displayed color of the colony, or the like. Non-colony pixels 206 that lie in the selected intensity range (and thus are not masked), but that are not identified as part of a colony, also may be displayed, may be masked, or may be pseudocolored or marked differently, among others.

IV. Methods of Colony Identification/Isolation

This section describes exemplary methods of identifying and/or isolating spectrally distinct colonies. The steps described in this section may be performed in any suitable combination and order and may be combined with and/or or performed with any other suitable steps or apparatus described elsewhere in the present disclosure.

A filter may be received in an optical path extending from a light source to a grayscale image detector. The filter may be placed in the optical path manually by a user or robotically by an instrument. The filter may be disposed under or over the instrument's stage.

Colonies including spectrally distinct first and second types may be received in the optical path. The colonies may be supported by a medium (e.g., a semi-solid medium) that is contained by a container. The container may be placed in the optical path manually or robotically, such that at least a portion of the container is illuminated by light from the light source. The container may be disposed in contact with the filter and/or may be disposed over or under the filter. The container may be received and/or placed in the optical path before or after the filter is received and/or placed in the optical path.

An image of the colonies may be obtained with the grayscale image detector. The filter may selectively decrease an average intensity of one type of colony relative to an average intensity of the medium and/or the other type of colony in the image.

A histogram of intensity values may be created for pixels in the image. The histogram may be displayed to a user. The histogram may have a medium peak composed of medium pixels, and one or more colony peaks composed of colony pixels. The medium peak may dominate in the displayed histogram; the colony peaks may or may not be tall enough to be visible to the user.

A subset of the pixels in the image may be selected from the histogram. The subset may represent an intensity range in the histogram, with the intensity range defined by only a lower limit, an upper limit, or both a lower limit and an upper limit. The subset of the pixels may be selected by a user with a graphical user interface or may be selected automatically from the histogram. If the medium peak dominates the histogram (and the colony peaks are not easily discernible), the intensity range may be selected with reference to the medium peak (e.g., an intensity range that is of lower intensity or of higher intensity than the medium peak).

A masked version of the image may be created from the subset of pixels. Colonies may be identified from the masked image. The masked image may display to the user only the subset of pixels, with the remaining pixels of the original image masked. The masked image may render pixels of identified colonies, or the colonies themselves, in the masked image as visibly distinct from the remaining pixels of the pixel subset selected from the histogram.

One or more identified colonies may be picked robotically. The number of colonies picked, and/or particular colonies picked, may be determined based on user input.

V. Selected Embodiments

This example presents selected embodiments of the present disclosure related to systems for identifying and isolating spectrally distinct colonies. The selected embodiments are presented as a series of numbered paragraphs.

1. A method of isolating colonies, the method comprising: (A) receiving a filter in an optical path extending from a light source to a grayscale image detector, the filter being configured to increase an intensity difference between a first type of colony and a spectrally distinct second type of colony; (B) receiving colonies including both types in the optical path; (C) obtaining an image of the colonies with the grayscale image detector; (D) identifying at least one of the types of colony in the image; and (E) picking robotically one or more colonies of the at least one type identified.

2. The method of paragraph 1, wherein the light source includes one or more lamps that collectively produce white light.

3. The method of paragraph 1 or paragraph 2, wherein the colonies are supported by a medium in a container, and wherein the step of receiving colonies causes the container to be supported by a stage.

4. The method of any of paragraphs 1 to 3, wherein the colonies are supported by a medium in a container, and wherein the step of receiving colonies includes a step of receiving the container on and in contact with the filter.

5. The method of any of paragraphs 1 to 4, wherein the first type of colony is blue and the second type of colony is white.

6. The method of any of paragraphs 1 to 5, wherein the colonies are supported by a semi-solid medium in a container, wherein the filter increases an intensity difference between the first type of colony and the medium in the image, compared to an absence of the filter.

7. The method of any of paragraphs 1 to 6, wherein the colonies are supported by a semi-solid medium in a container, wherein the filter selectively decreases an intensity of the first type of colony relative to the medium and the second type of colony in the image, compared to an absence of the filter.

8. The method of any of paragraphs 1 to 7, further comprising a step of creating a histogram of intensity values for pixels in the image, wherein the step of identifying is based on a subset of the pixels selected from the histogram by a user, an algorithm, or a combination of a user and an algorithm.

9. The method of paragraph 8, further comprising a step of displaying the histogram to a user with a graphical user interface, and a step of receiving input from the user via the graphical user interface, wherein the input from the user selects an intensity range from the histogram for one of the types of colony, with the intensity range defining the subset of the pixels.

10. The method of paragraph 9, wherein the step of receiving input includes a step of displaying a limit selector with the histogram to the user, and wherein the limit selector is adjustable by the user with respect to the histogram to separately define a lower limit and an upper limit of the intensity range.

11. The method of any of paragraphs 1 to 10, wherein the colonies are supported by a semi-solid medium in a container, wherein an average intensity of the first type of colony in the image is less than an average intensity of the medium and less than an average intensity of the second type of colony, wherein the step of identifying includes a step of identifying one or more colonies of the first type, and wherein the step of picking includes a step of picking at least one of the identified colonies of the first type.

12. A method of isolating colonies, the method comprising: (A) receiving a filter in an optical path extending from a light source to a grayscale image detector, the filter being configured to increase an intensity difference between a first type of colony and a spectrally distinct second type of colony; (B) receiving a container containing a semi-solid medium and colonies supported by the semi-solid medium in the optical path, wherein the colonies include least one colony of each of the first type and the second type; (C) obtaining an image with the grayscale image detector by detecting light received from the colonies and the medium, with the filter increasing the intensity difference in the image relative to an absence of the filter; (D) identifying at least one of the types of colony in the image; and (E) picking robotically one or more colonies of the at least one type identified.

13. A method of isolating colonies, the method comprising: (A) receiving a filter in an optical path extending from a light source to a grayscale image detector, the filter being configured to selectively decrease an intensity of a blue colony relative to a white colony; (B) receiving a medium and colonies supported by the medium in the optical path, wherein the colonies include at least one blue colony and at least one white colony; (C) obtaining an image with the grayscale image detector by detecting light received from the colonies and the medium, with the filter selectively decreasing an average intensity of one or more blue colonies relative to an average intensity of the medium and one or more white colonies; (D) creating a histogram of intensity values for pixels in the image; (E) identifying one or more blue colonies in the image based on a subset of the pixels selected from the histogram; and (F) picking robotically at least one of the blue colonies.

14. A system for identifying and isolating spectrally distinct colonies, comprising: (A) a detection system defining an optical path extending from a light source to a grayscale image detector; (B) a filter disposed in the optical path and configured to increase an intensity difference between a first type of colony and a spectrally distinct second type of colony; (C) a stage to support a container containing colonies including the first type and the second type; (D) a picking device; and (E) a data processing system configured (i) to receive an image of the colonies obtained by the image detector, (ii) to identify at least one of the types of colony in the image, and (iii) to instruct the picking device to robotically pick one or more colonies of the at least one type identified.

15. The system of paragraph 14, wherein the light source includes one or more lamps that collectively produce white light.

16. The system of paragraph 14 or paragraph 15, wherein the filter is provided by a removable filter assembly supported by the stage, and wherein the filter assembly includes at least one filtering sheet and a frame attached to the at least one filtering sheet.

17. The system of any of paragraphs 14 to 16, where the filter is configured to be located under and in contact with the container.

18. The system of any of paragraphs 14 to 17, wherein the filter is configured to increase an intensity difference between a blue colony and a white colony.

19. The system of any of paragraphs 14 to 18, wherein the filter is configured to increase an intensity difference between the first type of colony and a semi-solid medium in the image, relative to an absence of the filter.

20. The system of any of paragraphs 14 to 19, wherein the filter is configured to selectively decrease an average intensity of the first type of colony relative to an average intensity of semi-sold medium and relative to an average intensity of the second type of colony in the image, compared to an absence of the filter.

21. The system of any of paragraphs 14 to 20, wherein the data processing system is configured to identify at least one of the types of colony in the image based on user input that selects a subset of pixels in the image.

22. The system of any of paragraphs 14 to 21, wherein the data processing system includes a graphical user interface, wherein the data processing system is configured to create a histogram of intensity values for pixels in the image and to display the histogram to a user with the graphical user interface.

23. The system of paragraph 22, wherein the data processing system is configured to receive input from the user via the graphical user interface, wherein the input selects an intensity range from the histogram for one of the types of colony, and wherein the data processing system is configured to identify the one type of colony based on a subset of the pixels defined by the intensity range selected.

24. The system of paragraph 23, wherein the data processing system is configured to display a limit selector with the histogram to the user, and wherein the limit selector is configured to be adjustable by the user with respect to the histogram to separately define a lower limit and an upper limit of the intensity range.

VI. Exemplary System Configurations and Operating Procedures

Further aspects of an exemplary system, including methods and apparatus, for identifying and picking spectrally distinct colonies are described in the accompanying Appendix, which is a user guide that may be supplied to customers.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for identifying and isolating spectrally distinct colonies housed in a container, comprising:
   a detection system defining an optical path extending from a light source to a grayscale image detector;
   a spectral filter disposed in the optical path and configured to increase an intensity difference between a first type of colony and a spectrally distinct second type of colony, the spectral filter configured to be located under and in contact with the container housing the colonies;
   a stage to support a container containing colonies including the first type and the second type;
   a picking device; and
   a data processing system configured (i) to receive an image of the colonies obtained by the image detector, (ii) to identify at least one of the types of colony in the image, and (iii) to instruct the picking device to robotically pick one or more colonies of the at least one type identified.

2. The system of claim 1, wherein the light source includes one or more lamps that collectively produce white light.

3. The system of claim 1, wherein the spectral filter is provided by a removable filter assembly supported by the stage, and wherein the filter assembly includes at least one filtering sheet and a frame attached to the at least one filtering sheet.

4. The system of claim 1, where the spectral filter is configured to be located under and in contact with the container.

5. The system of claim 1, wherein the spectral filter is configured to increase an intensity difference between a blue colony and a white colony.

6. The system of claim 1, wherein the spectral filter is configured to increase an intensity difference between the first type of colony and a semi-solid medium in the image, relative to an absence of the spectral filter.

7. The system of claim 1, wherein the spectral filter is configured to selectively decrease an average intensity of the first type of colony relative to an average intensity of semi-sold medium and relative to an average intensity of the second type of colony in the image, compared to an absence of the spectral filter.

8. The system of claim 1, wherein the data processing system is configured to identify at least one of the types of colony in the image based on user input that selects a subset of pixels in the image.

9. The system of claim 1, wherein the data processing system includes a graphical user interface, wherein the data processing system is configured to create a histogram of intensity values for pixels in the image and to display the histogram to a user with the graphical user interface.

10. The system of claim 9, wherein the data processing system is configured to receive input from the user via the graphical user interface, wherein the input selects an intensity range from the histogram for one of the types of colony, and wherein the data processing system is configured to identify the one type of colony based on a subset of the pixels defined by the intensity range selected.

11. The system of claim 10, wherein the data processing system is configured to display a limit selector with the histogram to the user, and wherein the limit selector is configured to be adjustable by the user with respect to the histogram to separately define a lower limit and an upper limit of the intensity range.

\* \* \* \* \*